United States Patent [19]

Brancq et al.

[11] Patent Number: 5,164,014
[45] Date of Patent: Nov. 17, 1992

[54] PROCESS FOR THE MANUFACTURE OF A DIRECTLY COMPRESSIBLE STARCH FOR USE IN THE MANUFACTURE OF TABLETS, AND TABLETS OBTAINED

[75] Inventors: Bernard Brancq, Le Chesnay; Gérard Trouvé, Castres, both of France

[73] Assignee: Societe d'Exploitation de Produits pour les Industries Chimiques S.E.P.P.I.C., Paris, France

[21] Appl. No.: 523,500

[22] Filed: May 15, 1990

[30] Foreign Application Priority Data

May 16, 1989 [FR] France .................. 89 06385

[51] Int. Cl.⁵ .................... C08B 30/12; C08L 3/00
[52] U.S. Cl. ...................... 127/32; 127/65; 127/71; 106/213; 106/214
[58] Field of Search ............ 127/32; 106/213, 214

[56] References Cited

U.S. PATENT DOCUMENTS

| | | | |
|---|---|---|---|
| 2,749,259 | 6/1956 | Evans et al. | 127/32 |
| 2,929,748 | 3/1960 | Schwandt | 127/71 |
| 3,622,677 | 11/1971 | Short et al. | 127/32 |
| 4,155,884 | 5/1979 | Hughes | 106/213 |

FOREIGN PATENT DOCUMENTS

| | | |
|---|---|---|
| 2134510 | 12/1972 | France . |
| 1462633 | 1/1977 | United Kingdom . |
| 2093052 | 8/1982 | United Kingdom . |

OTHER PUBLICATIONS

C. E. Bos, et al., Pharmaceutisch Weekblad Scientific Edition, vol. 9, 1987, pp. 274-282, "Native Starch in Tablet Formulations".

Primary Examiner—Theodore Morris
Assistant Examiner—P. L. Hailey
Attorney, Agent, or Firm—Blum Kaplan

[57] ABSTRACT

The present invention relates to a process for the preparation of grains of starch, which comprises granulating a mixture obtained by spraying 1 to 20%, and preferably 2 to 6% by weight, of a starch paste obtained from native starch under mild conditions, on to 99 to 80% by weight of grains of native starch, and drying, grinding and sieving the resulting product to give aggregates (grains) having a mean particle size of between 100 and about 500 μm.

18 Claims, No Drawings

PROCESS FOR THE MANUFACTURE OF A DIRECTLY COMPRESSIBLE STARCH FOR USE IN THE MANUFACTURE OF TABLETS, AND TABLETS OBTAINED

Among the pharmaceutical forms in which therapeutic active principles are administered, the tablet occupies a particularly important position. These tablets are produced by compressing mixtures which contain, in addition to the active priniple or principles, one or more excipients making it possible to obtain tablets having the desired properties. Of these excipients, one of the most commonly used is starch.

Native starch (which can have very diverse origins) takes the form of grains with a mean diameter of a few tens of microns (generally 5 to 40 μm); this native starch has poor flow properties, is very difficult to compress and produces tablets of insufficient hardness.

It has been proposed to modify this native starch in order to improve its properties; the modifications described are of two types:
one type consists in making chemical modifications to the starch or to the surface of the grains of starch, leading to products which no longer comply with the "starch" monograph in the pharmacopeias; an example of this type of product is described in European patent 159 631;
the other type consists in making physical modifications which tend to partially gelatinize the surface of the grains of starch by passing them over heated rollers or subjecting them to high pressures in the presence of water; modifications of this type are described in U.S. Pat. Nos. 3,622,677 and 4,072,535; these patents describe the manufacturing process and the use of the starch, which is taken for the purpose of comparison in the Examples of the present patent application.

The products obtained by physical modification belong to the class of the "pregelatinized starches"; they often have inadequate flow properties and a poor disintegrating power, but an improved compressibility.

It has also been recommended to produce pastes by mixing grains of native starch with starch paste of relatively high viscosity, and forcing this mixture through the meshes of a sieve. However, the results obtained show that this method does not afford a substantial improvement in the properties of the native starch compared with the known commercial starches, whether the proportion of starch paste be low (cf. Pharm. WEEKBLATT, 9, (5), 1987, p. 274) or high (cf. U.S. Pat. No. 3,171,747).

The aim of the present invention is to produce granules of directly compressible starch which, compared with the starches described, have a particle size appropriate for homogeneous mixing with active principles, and appreciably improved properties as regards especially the particle size, flow, compressibility and rate of disaggregation of the tablets obtained.

The process according to the invention comprises granulating a mixture obtained by spraying 1 to 20%, and preferably 2 to 6% by weight, of a starch paste obtained from native starch under mild conditions, on to 99 to 80% by weight of grains of native starch, and drying and then, if appropriate, grinding and sieving the resulting product to give aggregates of grains of starch, called granules, having a mean particle size of between about 100 and about 500 μm.

In the process according to the invention, the "starch paste" is obtained from starch under "mild conditions". It is known that starch paste is very generally obtained by heating an aqueous dispersion of native starch. The degree of degradation of the starch depends on the heating rate, the temperature reached and the heating time; the aim of the invention is to employ mild conditions, i.e. gradual heating, a maximum temperature not exceeding about 85° C. and a heating time of the order of 15 to 45 min.

The resulting starch paste takes the form of an aqueous solution whose concentration (of starch in the paste) is of the order of 2 to 10%, preferably 5 to 8% by weight, and whose viscosity is less than 1500 mPa.s at 85° C. for a starch concentration of 5%. These aqueous solutions are thus sufficiently fluid to be able to be sprayed easily.

It has been possible to demonstrate two complementary characteristics of this starch paste which make it possible to obtain final products having optimum properties:
on the one hand, it is desirable for the starch paste to be used as soon as possible after it has been prepared; spraying will therefore be carried out using the hot solution (temperature equal to at least 60° C.) obtained at the end of the starch preparation process;
on the other hand, it is desirable for the starch paste to be obtained from the same native starch (or at least from a starch having the same origin) as that on to which said paste will be sprayed.

Granulation is carried out in an apparatus of the granulating mixer type (DIOSNA, LODIGE, GUEDU, FIELDER) or in any other apparatus having the same characteristics.

The agitator of the apparatus is started up and the hot starch paste is then pumped in and sprayed on to the moving grains of starch. After all the paste has been introduced, agitation is maintained for a sufficient time to give a non-sticky, homogeneous, granulated moist mass not containing any large non-friable agglomerates. During the last stage of granulation, it is desirable to start up the decaking device which is available on some of the apparatuses mentioned.

The granules obtained in the granulation operation are dried in a conventional drying apparatus, which can be a ventilated oven, a vacuum oven or a fluidized air bed. Preferably, the temperature of the ambient air in the drying device must not exceed 90° C.

A variant of the process consists in carrying out the granulation and drying in a single step in a fluidized air bed equipped with a spraying device, or in a granulator-dryer, for example of the type proposed by MORRITZ.

If appropriate, the dry granules obtained are then ground in a conventional mill (for example a hammer, knife or ball mill) or by the action of a rasp; this grinding must be carried out in such a way as to give, after sieving, granules having a mean particle size of about 100 to 500 μm.

The dry granules obtained by carrying out the process according to the invention have a particular structure which can be described schematically in the following manner: said granules are formed by the surface and point adhesion, by means of the starch paste, of several (for example 100 to 1000) grains of native starch, these grains of native starch not showing in themselves a substantial modification of their surface structure.

On compression under 20 daN, these granules, which have a mean particle size of between about 100 and 500

μm, give tablets having a hardness of at least about 50N and disintegrating in water in less than 5 min.

The process described in the present invention makes it possible to obtain a directly compressible starch complying with the "pregelatinized starch" monograph in the various pharmacopeias. Compared with the products existing on the market, this starch is characterized by:

very good flow properties, ensuring an excellent uniformity of weight of the tablets,
a good compressibility,
a particularly high disintegrating power.

The starch obtained can of course be used for the known applications of native starch and especially for the preparation of tablets; for this purpose, said starch is used by itself or with the other known excipients (and additives) used.

The following non-limiting Examples illustrate the invention.

EXAMPLE 1

Manufacture of a pilot batch of compressible starch

Starch paste 567 g of CODEX maize starch (Fleurine 3401-CERESTAR) are poured into 10.31 l of cold water, with stirring (Raynerie stirrer equipped with a deflocculator). The dispersion is heated gradually for 1 h, until the temperature reaches 85° C., and is then kept at this temperature for 30 min. Water is added to adjust for evaporation losses. The 5% solution obtained has a viscosity of the order of 770 mPa.s at 85° C.

Granulation 20 kg of Fleurine 3401 are deposited in a DIOSNA model V 100 granulator. The agitator of the granulator is started up (speed 1) and the paste is pumped in by means of a peristaltic pump in 2.5 min. Agitation is maintained under the same conditions for a total of 10 min and the decaking device is then run for a further 4 min (speed I).

The grains obtained are dried in a 240 MEMMERT ventilated oven at 80° C. until the residual moisture content is 12%.

They are then ground in a TORNADO mill (Sharples, Stokes, Rueil Malmaison) equipped with a 355 μm fine screen.

Characteristics of the granules obtained

These are summarized in Table 1. The methods of measurement are described in the references below:
Guyot J. C., Delacourte A., Marle B. Drug Dev. Ind. Pharm. 12, 1869–1884 (1986)
Guyot J. C. S.T. Pharma. 7, 10, 551–559 (1978)
Delacourte A., Guyot J. C., Traisnel M. S.T. Pharma. 11, 3, 131–140 (1982)

Formulations

Two formulations containing active principles were studied:

| FORMULATION 1: | Crystalline aspirin | 80% |
|---|---|---|
| | Starch | 20% |

-continued

| FORMULATION 2: | Ascorbic acid | 62% |
|---|---|---|
| | Starch | 32.5% |
| | Stérotex ® | 2% |
| | Aérosil ® | 0.5% |

The characteristics of the tablets obtained are given in Table 2.

EXAMPLE 2

3.5 kg of a starch paste containing 5.5% of starch are manufactured by the process described in Example 1.

This paste is poured, in 1 min, into the DIOSNA granulator containing 7 kg of Fleurine 3401. Granulation is carried out as described in Example 1.

The grains obtained are dried in a fluidized air bed at 80° C. (Aeromatic STREA 1) to a final moisture content of 12%, and then ground as described in Example 1.

The characteristics of the grains are given in Table 1.

EXAMPLE 3

78 kg of a 5.5% starch paste are manufactured by slowly heating a dispersion of Fleurine 3401 in water for 2 h until the temperature reaches 85° C. This temperature is maintained for 30 min and the paste is then pumped, in 11 min, into a 600 l DIOSNA granulator containing 150 kg of Fleurine 3401.

Agitation of the DIOSNA (speed 1) is maintained for a total of 21 min, after which decaking is carried out for a further 4 min at speed 1.

The grains obtained are dried in a vacuum oven at 80° C. under about 5000 Pa for 14 h until the residual moisture content reaches 11%. They are then ground as described above.

The characteristics of the grains obtained and of the formulations prepared are given in Tables 1 and 2.

EXAMPLE 4

Production of grains by granulation-drying in a fluidized air bed 500 g of CODEX maize starch are placed in an Aeromatic STREA 1 air bed. The flow rate of sustaining air is set at 120 m³/h. The air inlet temperature is 20° C. and the outlet temperature is 80° C.

600 g of a 5% starch paste are sprayed on to the grains of starch by means of a spray nozzle placed in the "low" position on the apparatus (flow rate of paste: 10 g/min, pressure of spraying air: 105 Pa). Dry granules with a moisture content of 3.5% are thus obtained in a single step.

The particle size distribution is as follows:
12% < 90 μm
23% between 90 and 125 μm
35% between 125 and 180 μm
23% between 180 and 250 μm
7% > 250 μm The flow time of these granules is 13 s.

A tablet prepared from these granules has a hardness of 50N for an applied force of 2000 daN.

A hardness of 90N was measured with grains obtained under the same conditions but having a residual moisture content of 12%.

TABLE 1

CHARACTERISTICS OF THE GRAINS OF STARCH ACCORDING TO THE INVENTION COMPARED WITH A COMMERCIAL STARCH

| STARCH (1500) | EXAMPLE 1 | EXAMPLE 2 | EXAMPLE 3 | COMMERCIAL (Starch 1500) |
|---|---|---|---|---|
| Particle size distribution % | | | | |
| $\phi > 315$ μm | 25 | 16 | 10 | 0–5 |
| $200 < \phi < 315$ μm | 25 | 16 | 30 | |
| $125 < \phi < 200$ μm | 23 | 25 | 33 | 5–30 |
| $80 < \phi < 125$ μm | 12 | 24 | 22 | |
| $\phi < 80$ μm | 15 | 19 | 5 | 55–35 |
| Flow time (s) | 3.2 | 3.5 | 3 | ∞ |
| Tap volume (ml) | 18 | 22 | 18 | |
| Applied force (daN) | 2030 | | 2194 | 2140 |
| Hardness (N) | 100 | | 107 | 88 |
| Cohesion index | 203 | 166 | 205 | 242 |
| Friability (%) | 0.2 | 1.1 | 0.4 | 1 |

TABLE 2

CHARACTERISTICS OF THE FORMULATIONS PREPARED WITH A COMMERCIAL STARCH AND THE STARCH ACCORDING TO THE INVENTION

| STARCH | EXAMPLE 1 | EXAMPLE 3 | COMMERCIAL |
|---|---|---|---|
| FORMULATION 1 | | | |
| Applied force (daN) | 2020 | 2080 | 2320 |
| Hardness (N) | 73 | 78 | 67 |
| Cohesion index | 277 | 260 | 346 |
| Friability (%) | 1.0 | 0.9 | 1.22 |
| Uniformity of weight of the tablets (%) | 1.8 | 1.7 | 1.5 |
| Disintegration time (min) | 1 | <1 | 6.5 |
| FORMULATION 2 | | | |
| Applied force (daN) | 1686 | 2140 | 1741 |
| Hardness (N) | 74 | 91 | 74 |
| Cohesion index | 227 | 235 | 236 |
| Friability (%) | 0.5 | 0.6 | 0.8 |
| Uniformity of weight | 1.3 | 1.3 | 2.9 |
| Disintegration time (min) | 3 | 3 | 13 |

What is claimed is:

1. A process for the preparation of granules of directly compressible starch which comprises:
   a) preparing a starch paste by heating gradually an aqueous dispersion of native starch at a maximum temperature not exceeding about 85° C. and a heating time of about 15 to about 45 minutes;
   b) granulating between about 99% to about 80% by weight of grains of native starch with about 1 to about 20% by weight of the starch paste obtained in step a); and
   c) drying the wet mass thus obtained to a moisture content sufficient to yield granules which are directly compressible and grinding and sieving to yield aggregates having a mean particles size of between about 100 and about 500 μm.

2. The process according to claim 1, wherein the concentration of starch in the paste is between about 2 and about 10% by weight.

3. The process according to claim 1, wherein the concentration of starch in the paste is between about 5 and about 8% by weight.

4. The process according to claim 1, wherein the starch paste has a viscosity of less than about 1500 mPa.s at about 85° C. for a solution containing about 5% by weight.

5. The process according to claim 1, wherein the starch paste used is obtained from the same native starch with which it is granulated.

6. The process according to claim 1, wherein in the granulation step b), the starch paste is sprayed onto the grains of native starch.

7. The process according to claim 1, wherein in the granulation step b), the starch paste is poured onto the grains of native starch.

8. A process for the preparation of granules of directly compressible starch which comprises:
   a) preparing a starch paste by heating gradually an aqueous dispersion of native starch at a maximum temperature not exceeding about 85° C. and a heating time of about 15 to about 45 minutes;
   b) granulating between about 98% to about 96% by weight of grains of native starch with about 2 to about 4% by weight of the starch paste obtained in step a); and
   c) drying the wet mass thus obtained to a moisture content sufficient to yield granules which are directly compressible and grinding and sieving to yield aggregates having a mean particles size of between about 100 and about 500 μm.

9. A process for the preparation of granules of directly compressible starch which comprises:
   a) preparing a starch paste by heating gradually an aqueous dispersion of native starch at a maximum temperature not exceeding about 85° C. and a heating time of about 15 to about 45 minutes;
   b) granulating between about 98% to about 96% by weight of grains of native starch with about 2 to about 4% by weight of the starch paste obtained in step a) and used at a temperature above about 60° C.; and
   c) drying the wet mass thus obtained to a moisture content sufficient to yield granules which are directly compressible and grinding and sieving to yield aggregates having a mean particles size of between about 100 and about 500 μm.

10. The process according to claim 9, wherein the concentration of starch in the paste is between about 2 and about 10% by weight.

11. The process according to claim 9, wherein the starch paste used is obtained from the same native starch with which it is granulated.

12. The process according to claim 9, wherein in the granulation step b), the starch paste is sprayed onto the grains of native starch.

13. The process according to claim 9, wherein in the granulation step b), the starch paste is poured onto the grains of native starch.

14. Novel starch granules suitable for compression into tablets, comprising starch granules prepared by the mutual adhesion of grains of native starch by means of starch paste, which have a mean particle size of between about 100 and about 500 μm, which give, on compression under about 20 daN, tablets having a crushing strength of at least about 50N, and which disintegrate in water in less than about 5 minutes.

15. The novel starch granules of claim 14, wherein the mutual adhesion of grains of native starch is point adhesion.

16. Tablets which contain the novel starch granules of claim 15 as the excipient.

17. A process for the preparation of granules of directly compressible starch which comprises:
   a) preparing a starch paste by heating gradually an aqueous dispersion of native starch at a maximum temperature not exceeding about 85° C. and a heating time of about 15 to about 45 minutes;
   b) granulating between about 99% to about 80% by weight of grains of native starch with about 1 to about 20% by weight of the starch paste obtained in step a); and
   c) drying the wet mass thus obtained to a residual moisture of 11-12% and grinding and sieving to yield aggregates having a mean particles size of between about 100 and about 500 μm.

18. A process for the preparation of granules of directly compressible starch which comprises:
   a) preparing a starch paste by heating gradually an aqueous dispersion of native starch at a maximum temperature not exceeding about 85° C. and a heating time of about 15 to about 45 minutes;
   b) granulating between about 98% to about 96% by weight of grains of native starch with about 2 to about 4% by weight of the starch paste obtained in step a); and
   c) drying the wet mass thus obtained to a residual moisture of 11-12% and, grinding and sieving to yield aggregates having a mean particles size of between about 100 and about 500 μm.

* * * * *